US007342232B2

(12) United States Patent
Xie et al.

(10) Patent No.: US 7,342,232 B2
(45) Date of Patent: Mar. 11, 2008

(54) DEVICE AND METHOD FOR DIGITIZING PET RADIATION EVENTS

(75) Inventors: Qingguo Xie, Wuhan (CN); Chien-Min Kao, Chicago, IL (US); Zekai Hsiau, Taipei (TW); Chin-Tu Chen, Chicago, IL (US)

(73) Assignee: National Health Research Institutes, Jhunan Township, Miali County (TW)

( * ) Notice: Subject to any disclaimer, the term of this patent is extended or adjusted under 35 U.S.C. 154(b) by 222 days.

(21) Appl. No.: 11/097,153

(22) Filed: Apr. 4, 2005

(65) Prior Publication Data

US 2006/0000979 A1    Jan. 5, 2006

Related U.S. Application Data

(60) Provisional application No. 60/558,710, filed on Apr. 2, 2004.

(51) Int. Cl.
    *G01T 1/164*    (2006.01)
(52) U.S. Cl. .................................. 250/363.03
(58) Field of Classification Search ........... 250/363.03, 250/363.04, 353.05
    See application file for complete search history.

(56) References Cited

U.S. PATENT DOCUMENTS

| 4,531,058 | A | * | 7/1985 | Burnham et al. ...... 250/363.03 |
| 4,675,526 | A | * | 6/1987 | Rogers et al. ......... 250/363.02 |
| 5,083,026 | A | * | 1/1992 | Elbaum .................... 250/369 |
| 5,608,221 | A | * | 3/1997 | Bertelsen et al. ...... 250/363.03 |
| 5,907,156 | A | * | 5/1999 | Nishizawa et al. .... 250/370.01 |
| 6,057,551 | A | * | 5/2000 | Tararine ................ 250/363.03 |
| 6,232,604 | B1 | * | 5/2001 | McDaniel et al. ..... 250/363.03 |
| 6,376,841 | B1 | * | 4/2002 | Petrillo et al. ......... 250/363.03 |

* cited by examiner

*Primary Examiner*—David Forta
*Assistant Examiner*—Casey Bryant
(74) *Attorney, Agent, or Firm*—Finnegan, Henderson, Farabow, Garrett & Dunner LLP (57) ABSTRACT

A device and method used in the high resolution Positron Emission Tomography (PET) systems for digitizing radiation events for a scintillation camera and a data acquisition system. The device comprises a scintillation digitizer, including a plurality of comparators and amplifiers, two ADCs, and an analyzer for resolving the digital values of radiation events. The method comprises comparing a plurality of analog electric pulses generated upon radiation event detections with a reference voltage corresponding to an energy level of interest, amplifying all of the signals with two groups of coefficients, summing the two groups of amplified signals, digitizing the summed signals, and analyzing the digitized sums to determine digital values corresponding to a plurality of the radiation events.

7 Claims, 5 Drawing Sheets

DEVICE AND METHOD FOR DIGITIZING PET RADIATION EVENTS

CROSS-REFERENCE TO RELATED APPLICATIONS

This application is based upon and claims the benefit of priority from prior Provisional Application No. 60/558,710, filed on Apr. 2, 2004, the entire contents of which are incorporated herein by reference.

TECHNICAL FIELD

This invention relates to the field of positron emission tomography (PET). More particularly, the present invention relates to signal processing devices and methods used in PET front-end electronics.

BACKGROUND

Positron emission tomography (PET) is a technique used in clinical medicine and biomedical research to create images that show anatomical structures as well as how certain tissues are performing their physiological functions. Radioactive nuclei are introduced into the body as labels on tracer molecules. These nuclei emit positrons which collide with electrons in the tissue. Each collision constitutes an annihilation event that may result in two gamma photons. By detecting the gamma photons and processing the result with image processing tools, an image of the activity in the tissue can be produced to display the physiological functions.

In positron emission tomography (PET) systems, a scintillation light pulse generated upon the interaction of a photon from the annihilation event with a scintillator is collected by photomultiplier tubes (PMT), or avalanche photodiodes (APD), and converted into a charge pulse. Hamamatsu Photonics K.K. Electron Tube Center, *Fundamental and Applications of Photomultiplier Tube*, JP:Hamamatsu Photonics K.K, 1995, the contents of which are hereby incorporated by reference, provides further details on the PMT. The charge pulse is often amplified and filtered to form a new voltage pulse that has a peak amplitude proportional to the area under the original scintillation light pulse, and hence proportional to the amount of photon energy that is deposited in the scintillator during the interaction. The peak amplitude is then sampled and converted into digital data by use of analog-to-digital converters (ADCs) for subsequent processing. An event time is typically obtained by using constant fraction discriminators (CFDs). Depth of Interaction Detector Block for High Resolution Positron Emission Tomography (U.S. Pat. No. 6,288,399 to Andreaco et al.), provides further details on implementation of PET detectors.

Efforts to achieve higher spatial resolution and a larger imaging volume have led to use of more and more small scintillators in PET design. Since every scintillator output needs to be separately processed, the number of ADC channels in a modern PET system is rapidly increasing. In addition, as faster scintillators and a 3D imaging mode are more widely used, high-speed ADCs are often desirable. However, a PET system that employs a large number of high-speed ADCs not only consumes a large amount of power, but also is often too expensive for many applications.

SUMMARY

Consistent with embodiments of the present invention, methods and devices may be provided for digitizing Gamma ray energy and characterizing peak time and decay time constant with a minimum number of ADCs.

Consistent with the present invention, a method is performed by a PET system for digitizing radiation events. The method includes combining a group of analog voltage pulses generated by PET detectors to create fewer analog signals than the number of analog voltage pulses in the group, digitizing the created analog signals, and analyzing the digitized signals to obtain a digitized voltage value of each individual analog voltage pulse in the group.

Also consistent with the invention, a device may provide electronic means to carry out the method of digitizing PET radiation events by using minimum number of ADCs. The device may include plural sets of amplifiers, each set of amplifiers coupled to receive a same group of analog voltage pulses generated by PET detectors; a plurality of adders, each coupled to receive outputs from one set of amplifiers of the plural sets of amplifiers and to sum the outputs into one signal; a plurality of ADCs, each ADC coupled to receive an output of one of the adders to convert the output into digital form; and an analyzer coupled to receive outputs of the plurality of ADCs to determine digital voltage value of each individual voltage pulse in the group of analog voltage pulses.

It is to be understood that both the foregoing general description and the following detailed description are exemplary and explanatory only and are not restrictive of the invention, as claimed.

BRIEF DESCRIPTION OF THE DRAWINGS

The accompanying drawings, which are incorporated in and constitute a part of this specification, illustrate several aspects of the invention and together with the description, serve to explain the principle of the invention. In the drawings.

DETAILED DESCRIPTION

Reference will now be made in detail to the exemplary aspects of the invention, examples of which are illustrated in the accompanying drawings. Wherever possible, the same reference numbers will be used throughout the drawings to refer to the same or like parts.

Figure 1:
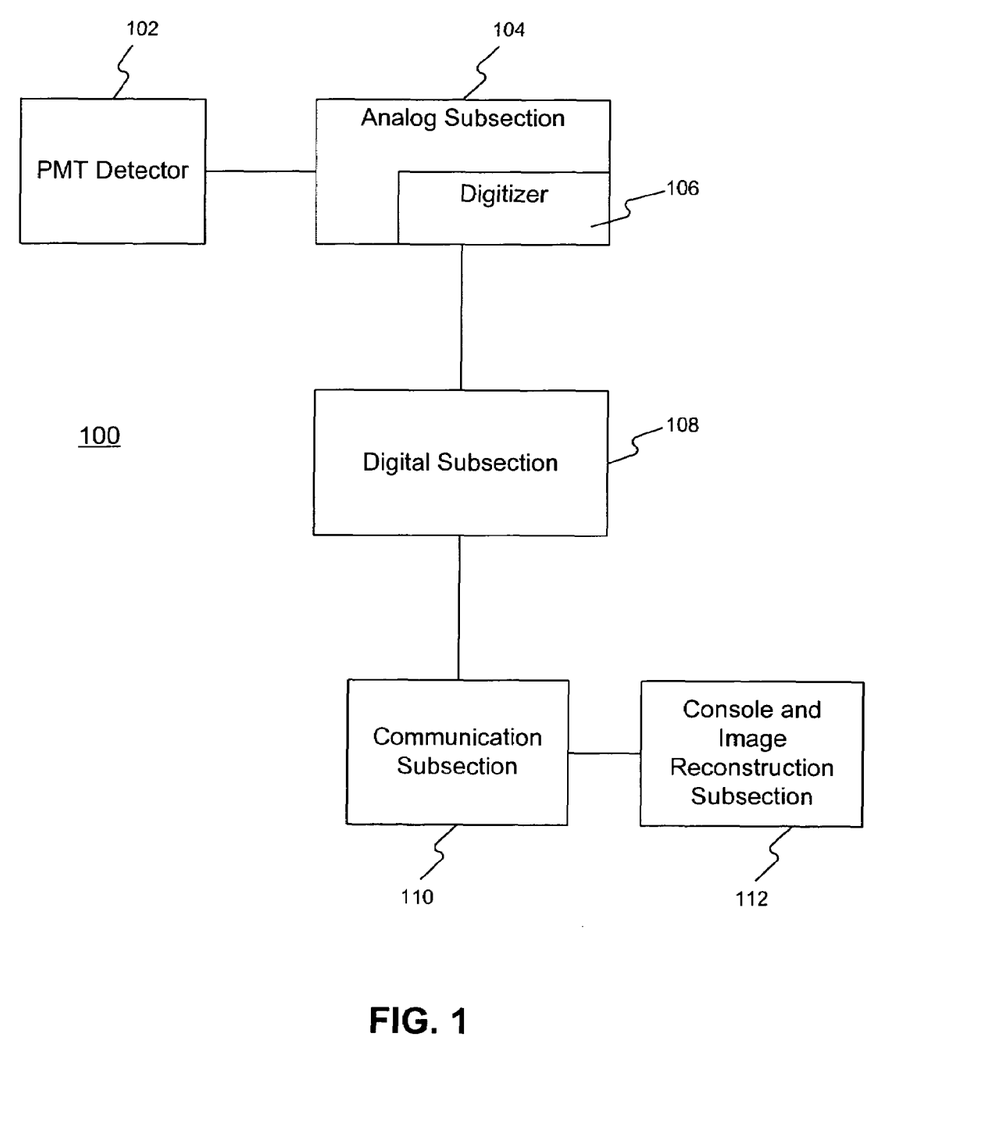
FIG. 1 is a block diagram of an exemplary PET system consistent with the present invention.

FIG. 1 illustrates an exemplary PET system 100 consistent with the present invention. PET system 100 includes a PMT detector 102 to detect light pulses from a scintillator (not shown) and convert the detection result into a charge pulse. Detector 102 includes circuitry for amplifying and filtering the charge pulse to provide a voltage pulse. An analog subsection 104 of PET system 100 receives and processes the voltage pulse. Analog subsection 104 includes a digitizer 106 to digitize the voltage pulse and to provide, in digital form to a digital subsection 108, parameters of the voltage pulse that are relevant to PET event detection. Digital subsection 108 performs all of the digital signal processing procedures needed by a PET system, and the results of the digital processing by digital subsection 108 can be further transmitted to other systems by a communication subsection 110, or displayed on a console and image reconstruction subsection 112.

Communication subsection 110 may be any appropriate type of communication system or device used to transmit the results of the digital processing. Console and image reconstruction subsection 112 may include any appropriate type of console device or computer system used to display the results of the digital processing from Digital subsection 108.

Figure 2:
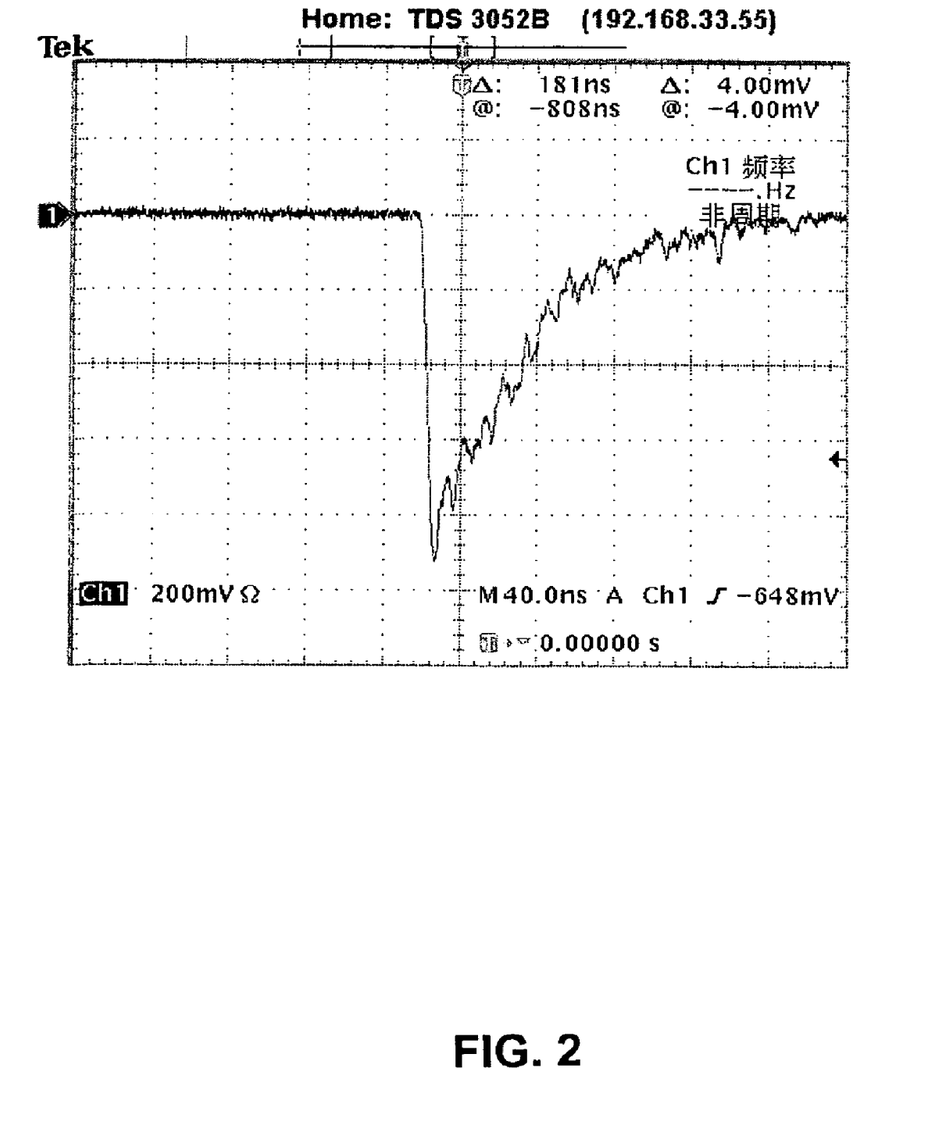
FIG. 2 is a diagram of an exemplary voltage pulse generated by an LSO/PMT detector.

FIG. 2 shows an exemplary voltage pulse generated by a PET detector 102, in particular, a lutetium oxyorthosilicate crystal coupled PMT (LSO/PMT) detector, upon interaction of a gamma ray photon with the LSO. The pulse is measured across a resistor that is directly connected to the LSO/PMT detector. The illustrated exemplary voltage pulse was sampled by using a digital oscilloscope at a 5 GHz sampling rate. The peak time and decay constant observed from numerous such pulses are about 10 ns and 40-45 ns, respectively.

Figure 3:
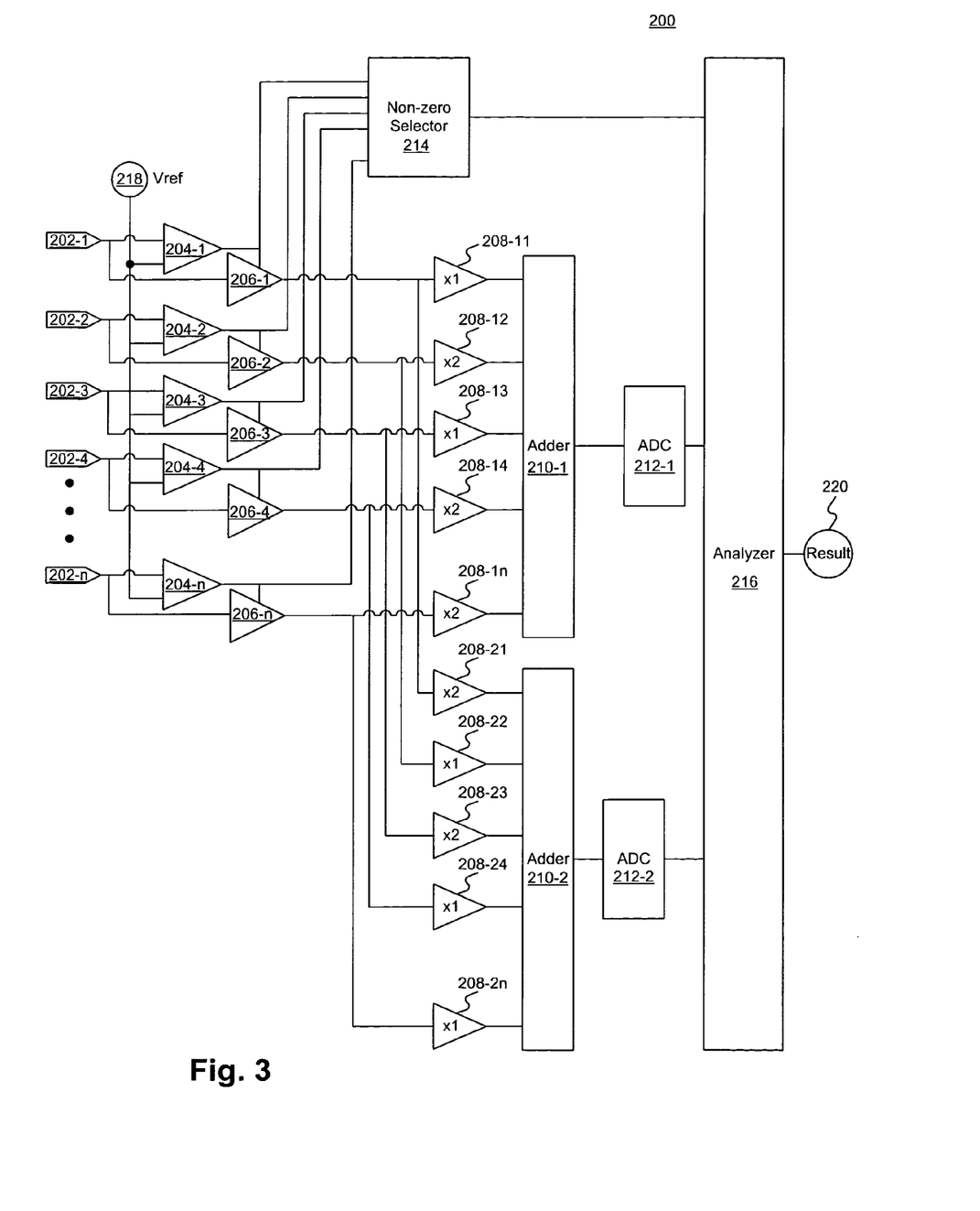
FIG. 3 is a block diagram of an exemplary digitizer of the system of the system of FIG. 1 consistent with the present invention.

FIG. 3 illustrates a block diagram of a digitizer 200 corresponding to digitizer 106 in FIG. 1. Digitizer 200 may be based on any appropriate type of mechanisms, such as application specific integrated circuit (ASIC), field programmable gate array (FPGA), and/or a combination of software programs and a microprocessor. As shown in FIG. 3, digitizer 200 comprises a plurality of inputs 202-1 to 202-*n*; a plurality of comparators 204-1 to 204-*n*; a plurality of gates 206-1 to 206-*n*; two sets of amplifiers, the first set including a plurality of amplifiers 208-11 to 208-1*n* and the second set including a plurality of amplifiers 208-21 to 208-2*n*; two adders 210-1 and 210-2; two analog-to-digital converters (ADCs) 212-1 and 212-2; a non-zero selector 214; an analyzer 216; a reference voltage input 218; and an output 220. It should be understood that the number of components, the reference voltage levels, and steps for performing the invention are exemplary and not intended to be limiting. The number of components or devices may be changed, the order of the components may be changed, the functionalities of components may be combined into different components without departing from the principle and scope of the present invention.

During operations of digitizer 200, inputs 202-1 to 202-*n* receive a plurality of analog voltage pulses $V_i(t)$ generated by PET detectors that need to be processed. The total number n of analog voltage pulses is determined based on the actual algorithms used, which will be explained in detail in the descriptions corresponding to FIGS. 4 and 5. The received analog voltage pulses may or may not be pre-amplified. First inputs of comparators 204-1 to 204-*n* are coupled to receive the plurality of analog voltage pulses from the inputs 202-1 to 202-*n*, respectively. Second inputs of comparators 204-1 to 204-*n* are coupled to receive a reference voltage $V_{ref}$ from input 218. The reference voltage $V_{ref}$ is a pre-determined voltage level of interest such that any input voltage pulse $V_i(t)$ lower than $V_{ref}$ is considered to have a zero magnitude and only an input voltage pulse $V_i(t)$ higher than or equal to $V_{ref}$ is considered as a valid detected event.

Inputs of gates 206-1 to 206-*n* are coupled to inputs 202-1 to 202-*n*, respectively, to receive the analog voltage pulses $V_i(t)$. Outputs of gates 206-1 to 206-*n* are coupled both to inputs of the first set of amplifiers 208-11 to 208-1*n*, respectively, and to inputs of the second set of amplifiers 208-21 to 208-2*n*, respectively. Gates 206-1 to 206-*n* are also coupled to be controlled by outputs of comparators 204-1 to 204-*n*, respectively. Each of comparators 204-1 to 204-*n* is configured to provided an output equal to the reference voltage $V_{ref}$ if the corresponding analog voltage pulse on the first input of the comparator is less than or equal to the reference voltage $V_{ref}$. If an output of a comparator equals the reference voltage $V_{ref}$, the gate corresponding to the comparator will be turned off under the control of the output of the comparator. Otherwise, the gate will be turned on to permit an analog voltage pulse on the input of the gate to reach two corresponding amplifiers. If the analog voltage pulse is greater than the reference voltage $V_{ref}$, then the output of the comparator is substantially equal to the analog voltage pulse, which is higher than the reference voltage $V_{ref}$.

Two sets of amplifiers 208-11 to 208-1*n* and 208-21 to 208-2*n* amplify the same plurality of analog voltage pulses separately according to different algorithms. Operations of the amplifiers 208-11 to 208-1*n* and 208-21 to 208-2*n* will be explained in detail below with reference to FIGS. 4 and 5. Adder 210-1 is coupled to receive all outputs of amplifiers 208-11 to 208-1*n*. Adder 210-1 sums all received outputs into one output signal. Similarly, adder 210-2 is coupled to receive all outputs of amplifiers 208-21 to 208-2*n*, and adder 210-2 sums all received outputs into one output signal. ADCs 212-1 and 212-2 are coupled to convert output signals from adders 210-1 and 210-2, respectively, into digital form. ADCs 212-1 and 212-2 are high-speed, high-precision analog-to-digital converters (ADCs). The precision of ADCs 212-1 and 212-2 is preferably higher than what is needed for converting any individual analog input voltage within the plurality of analog voltage pulses.

Non-zero selector 214 is coupled to receive outputs from comparators 204-1 to 204-*n* to determine whether a particular output is zero, which means whether an output is equal to the reference voltage $V_{ref}$. Non-zero selector 214 outputs the determined result in a suitable format, including but not limiting to a bit-mask representation. Analyzer 216 is coupled to receive digital outputs from ADCs 212-1 and 212-2 and non-zero selector 214. Using the digital outputs from ADCs 212-1 and 212-2, and the output from non-zero selector 214, analyzer 216 performs various arithmetic operations according to different algorithms that may be used to practice the present invention, details of which are explained in the descriptions corresponding to FIGS. 4 and 5. As a result of the arithmetic operations, analyzer 216 determines a digital value for each individual analog voltage pulse of the plurality of analog voltage pulses. Analyzer 216 then outputs the digital values corresponding to the individual analog voltage pulses on output 220. Output 220 provides digital signals to other digital signal processing units (not shown) for further PET signal processing. It is understood that all the components shown in FIG. 3 may be implemented individually or may be implemented on a single VLSI device such as ASIC, FPGA or FPAA. Computer software may also be used to achieve the same result when appropriately implemented.

Figure 4:
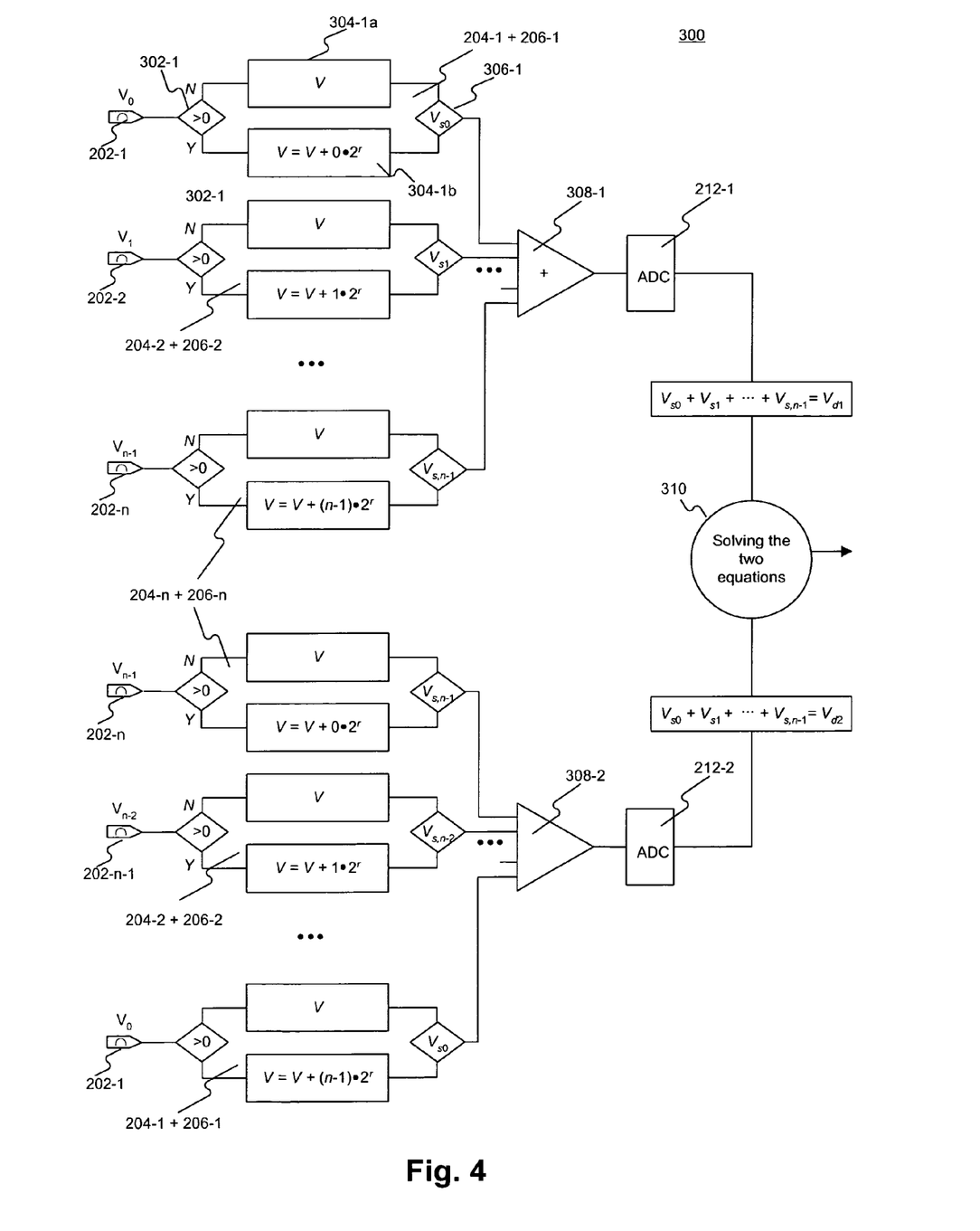
FIG. 4 illustrates an exemplary algorithm consistent with the present invention.

FIG. 4 is a diagram of logic 300 representing a non-limiting example of the operation of digitizer 106 in a manner consistent with the present invention. FIG. 4 shows receipt of analog voltage pulses $V_0, V_1, \ldots, V_{n-1}$ at inputs 202-1 to 202-*n*, respectively. The logical operations performed by comparators 204-2 and gates 206-2 are represented by logic blocks. For example, the test of whether an analog voltage pulse is greater than $V_{ref}$ is represented by logic such as logic block 302-1. More specifically, as previously explained, any voltage pulse $V_i(t)$ lower than $V_{ref}$ is considered to have a zero magnitude. Thus, each such voltage pulse having a magnitude lower than $V_{ref}$ is assigned a magnitude of zero resulting in the "N" (no) response when the assigned magnitude is tested as to whether it is greater than zero. Alternatively, if the magnitude of the voltage pulse is greater than or equal to $V_{ref}$, its actual value is compared to zero, and the result of the test is "Y" (yes).

In the case the test result is "N," the value V=0 (block 304-1a) is assigned to a computational term $V_{s0}$ (block 306-1). If the test result is "Y," the value V is determined as the actual value V of the voltage pulse amplified, e.g., by amplifier 208-11, to provide an amplified value of $V=V+0\times 2^r$ (block 304-1b). This amplified value is assigned to the computational term $V_{s0}$. Further details regarding the magnitude of amplification are provided below.

In FIG. 4, the computational terms $V_{s0}+\ldots+V_{s, n-1}$ are applied to functional blocks 308-1 and 308-2. Functional block 308-1 represents amplifiers 208-11 to 208-1n and adder 210-1, and functional block 308-2 represents amplifiers 208-21 to 208-2n and adder 210-2. Since, in general, the digital conversion performed by an ADC is done via quantization, an output value of an ADC does not correspond to a unique input value, but to a small range of input values. The resolution or precision of an ADC is thus the number of unique output values representing the analog input signal, and is generally represented by the number of bits. For an ADC with an s-bit precision, the ADC can have $2^s-1$ unique output values. The higher the precision of an ADC, the more unique output values it can have. In FIG. 4, m-bit precision ADCs are used in the illustrated embodiment. Among m bits, only r bits are required to convert any input analog voltage, where m is greater than r.

An integer k is defined such that k<m−r. A total number of n analog voltage pulses $V_0, V_1, \ldots, V_{n-1}$ may then be combined together as a group, where n=1, 2, 4, …, $2^k$. Accordingly, n inputs 202-1 to 202-n; n comparators 204-1 to 204-n; n gates 206-1 to 206-n; two sets of amplifiers, the first set including n amplifiers 208-11 to 208-1n and the second set including n amplifiers 208-21 to 208-2n; two adders 210-1 and 210-2; two analog-to-digital converters (ADCs) 212-1 and 212-2; a non-zero selector 214; an analyzer 216; a reference voltage input 218; and an output 220 are implemented to perform the logical operations represented in FIG. 4. If any input analog voltage pulse $V_i$ is lower than the reference voltage $V_{ref}$, the input analog voltage pulse $V_i$ is considered as a zero voltage, and is not involved in further processing. If any input analog voltage pulse $V_i$ is considered as a non-zero voltage, then a voltage of $i\times 2^r$ is added to the pulse $V_i$ by the corresponding amplifier 208-1i. This results in an amplified analog voltage pulse:

$$V_{s,i}=V_i+i\times 2^r,$$

where i=0, 1, …, n−1. The amplified voltage pulse is then applied to adder 210-1. The resulting summed signal from adder 210-1 is in the form of:

$$V_{d1}=V_{s0}+V_{s1}+\ldots+V_{s, n-1}, \quad (1)$$

where $V_{s0}$ is either $V_0=0$ or $V_0+0\times 2^r$, $V_{s1}$ is either $V_1=0$ or $V_1+1\times 2^r$, …, and $V_{s,n-1}$ is either $V_{n-1}=0$ or $V_{n-1}+(n-1)\times 2^r$, according to the logic described above.

The same input analog voltage pulse $V_i$ is, at the same time, processed by a second set amplifier 208-2n, but in a reversed sequence. Instead of adding a voltage of $i\times 2^r$, a voltage of $(n-1-i)\times 2^r$ is added by a corresponding amplifier 208-2n. In the case that the analog voltage pulse is greater than $V_{ref}$, this results in an amplified analog voltage pulse of:

$$V_{s,i}=V_i+(n-1-i)\times 2^r,$$

where i=0, 1, …, n−1. The amplified voltage pulse is then applied to adder 210-2. The resulting summed signal from adder 210-2 is in the form of:

$$V_{d2}=V_{s0}+V_{s1}+\ldots+V_{s, n-1} \quad (2)$$

where $V_{s0}$ is either $V_0=0$ or $V_0+(n-1)\times 2^r$, $V_{s1}$ is either $V_1=0$ or $V_1+(n-1)\times 2^r$, …, and $V_{s,n-1}$ is either $V_{n-1}=0$ or $V_{n-1}+0\times 2^r$.

The summed signals from adders 210-1 and 210-2, within functional blocks 308-1 and 308-2, respectively, are digitized by ADCs 212-1 and 212-2, respectively. The digitized results representing equations (1) and (2) are provided to analyzer 216 corresponding to logic block 310.

Analyzer 216 solves equations (1) and (2) to obtain digital values of individual analog pulses $V_0, V_1, \ldots, V_{n-1}$. It should be understood that equations (1) and (2) may be solved individually, or solved in combination. In a timing window, there may be only two variables are not less than $V_{ref}$. If there are more than two variables larger than $V_{ref}$, although less likely, all events in the timing window may be discarded. Further, equations (1) and (2) may be simplified by identifying the zero voltage pulse using non-zero selector 214.

Figure 5:
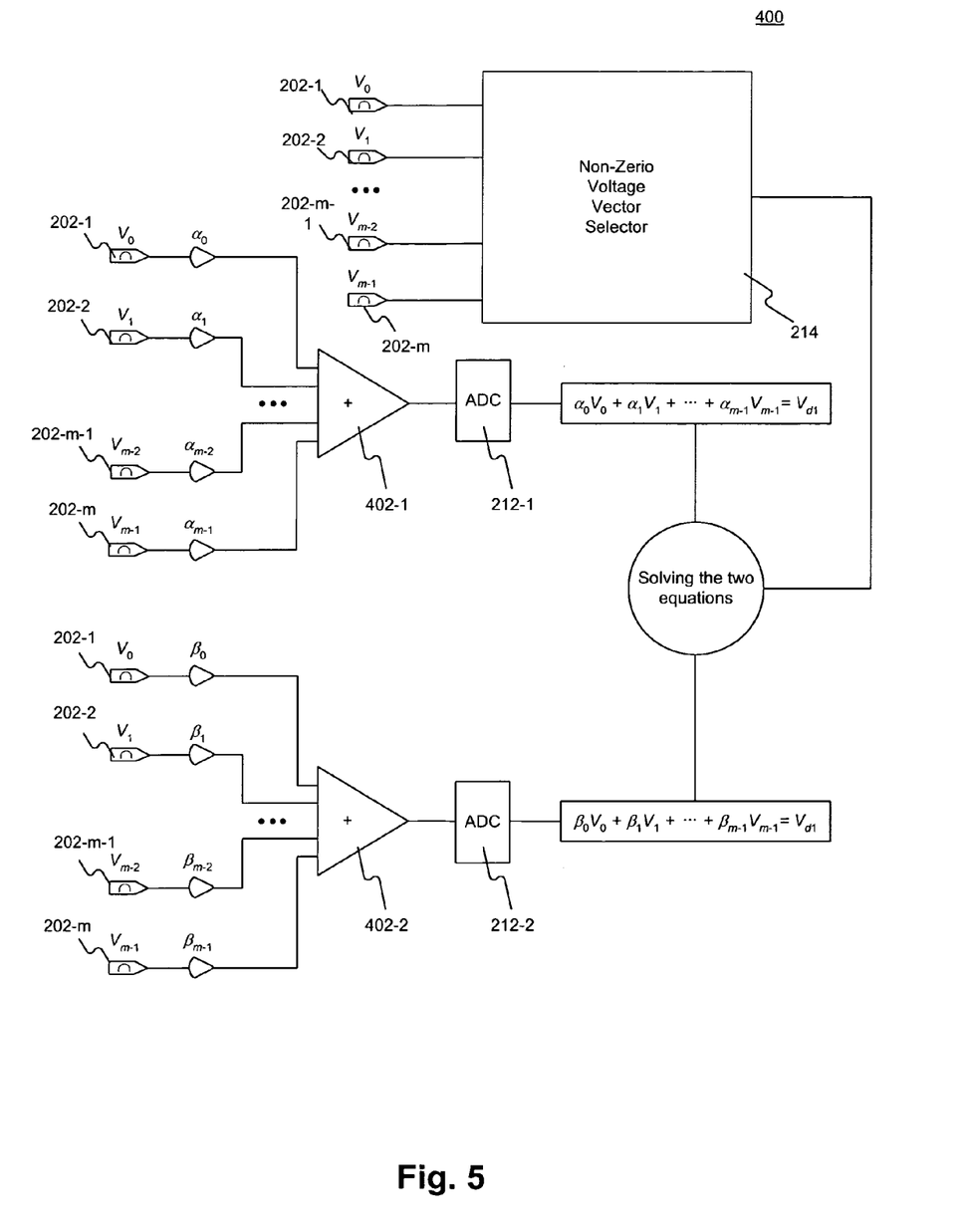
FIG. 5 illustrates another exemplary algorithm consistent with the present invention.

FIG. 5 is a diagram of logic 400 representing another non-limiting example of the operation of digitizer 106 in a manner consistent with the present invention. In FIG. 5, functional block 402-1 represents amplifiers 208-11 to 208-1n and adder 210-1, and functional block 402-2 represents amplifiers 208-21 to 208-2n and adder 210-2. In FIG. 5, m-bit precision ADCs are also used. A total number of m analog voltage pulses $V_d=[V_0, V_1, \ldots, V_{m-1}]$ may be received for processing, that is, n is equal to m. Accordingly, n number of inputs 202-1 to 202-n; n comparators 204-1 to 204-n; n gates 206-1 to 206-n; two sets of amplifiers, the first set including n amplifiers 208-11 to 208-1n and the second set including n amplifiers 208-21 to 208-2n; two adders 210-1 and 210-2; two analog-to-digital converters (ADCs) 212-1 and 212-2; a non-zero selector 214; an analyzer 216; a reference voltage input 218; and an output 220 are provided. The first set of amplifiers 208-11 to 208-1n apply a set of coefficients $\alpha_i=[\alpha_{0,i}, \alpha_{1,i}, \ldots, \alpha_{m-1,i}]^T$ to the input analog voltage pulses. As a result, outputs from ADC 212-1 can then be represented as:

$$V_d \cdot \alpha_i,$$

Similarly, the second set of amplifiers 208-21 to 208-2n apply a different set of coefficients $\beta_i=[\beta_{0,i}+\beta_{1,i}+\ldots+\beta^{m-1,i}]^T$ to the input analog voltage pulses. As a result, outputs from ADC 212-2 can be represented as:

$$V_d \cdot \beta_i.$$

Coefficient sets $\alpha_i$ and $\beta_i$ may be determined according to the structure of digitizer 200 or to the geometry of PET system 100. For example, $\alpha_i$ may be chosen as $\alpha_i=I+1$; and $\beta_i$ may be chosen as $\beta_i=m-i$. Therefore, analyzer 216 may determine a digital value of each individual analog voltage pulse by solving the following equations (3) and (4):

$$\alpha_0 V_0+\alpha_1 V_1+\ldots+\alpha_{m-1}V_{m-1}=V_{d1}, \quad (3)$$

$$\beta_0 V_0+\beta_1 V_1+\ldots+\beta_{m-1}V_{m-1}=V_{d2}, \quad (4)$$

Any zero input analog voltage pulse may be omitted from equations (3) and (4) with the information provided by non-zero selector 214, to simplify the computation. As explained above, in a timing window, there may be only two variables are not less than $V_{ref}$. If there are more than two variables larger than $V_{ref}$, although less likely, all events in the timing window may be discarded. Equations (3) and (4) may be solved similarly as to equations (1) and (2).

Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. A method for use in positron emission tomography (PET) for digitizing radiation events, comprising:
   combining a group of analog voltage pulses generated by PET detectors to create fewer analog signals than the total number of analog voltage pulses in the group;
   digitizing the created analog signals; and
   analyzing the digitized signals to obtain a digitized voltage value of each individual analog voltage pulse in the group,
   wherein the digitizing is performed by ADCs and the analyzing further comprises:
      defining the group of analog voltage pulses as $V_0$, $V_1, \ldots, V_{n-1}$, wherein $n=1, 2, 4, \ldots, 2^k$ and $k < m-r$, m and r being actual and required precision of the ADCs, respectively, and $m > r$;
      determining the created analog signals as $V_{d1} = V_{s0} + V_{s1} + \ldots + V_{s,\,n-1}$, wherein $V_{s,i} = V_i + i \times 2^r$, and $V_{d2} = V_{s0} + V_{s1} + \ldots + V_{s,\,n-1}$, wherein $V_{s,i} = V_i + (n-1-i) \times 2^r$;
      determining a digital value of each individual analog voltage pulse $V_i$ by solving equations $V_{d1} = V_{s0} + V_{s1} + \ldots + V_{s,\,n-1}$ and $V_{d2} = V_{s0} + V_{s1} + \ldots + V_{s,\,n-1}$; and
      outputting the resulting digital value of each analog voltage pulse.

2. A method for use in positron emission tomography (PET) for digitizing radiation events, comprising:
   combining a group of analog voltage pulses generated by PET detectors to create fewer analog signals than a total number of the analog voltage pulses in the group;
   digitizing the created analog signals; and
   analyzing the digitized signals to obtain a digitized voltage value of each individual analog voltage pulse in the group,
   wherein the combining further comprises
      amplifying the group of analog voltage pulses by adding to each analog voltage pulse in the group a voltage level determined based on a relative position of each analog voltage pulse in the group; and
      summing the amplified analog voltage pulses, and
   wherein the digitizing is performed by ADCs and the analyzing further comprises
      defining the group of analog voltage pulses as $V_0, V_1, \ldots, V_{m-1}$, a set of coefficients $\alpha_i = [\alpha_{0,i}, \alpha_{1,i}, \ldots, \alpha_{m-1,i}]^T$, and a set of coefficients $\beta_i = [\beta_{0,i} + \ldots + \beta_{m-1,i}]^T$, wherein m is an actual precision of the ADCs;
      determining the created analog signals as $V_{d1} = \alpha_0 V_0 + \alpha_1 V_1 + \ldots + \alpha_{m-1} V_{m-1}$, and $V_{d2} = \beta_0 V_0 + \beta_1 V_1 + \ldots + \beta_{m-1} V_{m-1}$;
      determining a digital value of each individual analog voltage pulse $V_i$ by solving equations $V_{d1} = \alpha_0 V_0 + \alpha_1 V_1 + \ldots + \alpha_{m-1} V_{m-1}$ and $V_{d2} = \beta_0 V_0 + \beta_1 V_1 + \ldots + \beta_{m-1} V_{m-1}$; and
      outputting the resulting digital value of each analog voltage pulse.

3. A method for use in positron emission tomography (PET) for digitizing radiation events, comprising:
   comparing each voltage pulse of a group of analog voltage pulses generated by PET detectors with a reference voltage of predetermined energy level of interest such that any analog voltage pulse higher than a reference voltage is kept and any analog voltage pulse lower than the reference voltage is set to zero;
   combining the group of analog voltage pulses to create fewer analog signals than a total number of the analog voltage pulses in the group,
   digitizing the created analog signals; and
   analyzing the digitized signals to obtain a digitized voltage value of each individual analog voltage pulse in the group,
   wherein the digitizing is performed by ADCs and the analyzing further comprises:
      defining the group of analog voltage pulses as $V_0$, $V_1, \ldots, V_{n-1}$, wherein $n = 1, 2, 4, \ldots, 2^k$ and $k < m-r$, m and r being actual and required precision of the ADCs, respectively, and $m > r$;
      determining the created analog signals as $V_{d1} = V_{s0} + V_{s1} + \ldots + V_{s,\,n-1}$, wherein $V_{s,i} = V_i + i \times 2^r$, and $V_{d2} = V_{s0} + V_{s1} + \ldots + V_{s,\,n-1}$, wherein $V_{s,i} = V_i + (n-1-i) \times 2^r$;
      removing the variables corresponding to analog voltage pulses set to zero;
      determining a digital value of each individual analog voltage pulse $V_i$ by solving equations $V_{d1} = V_{s0} + V_{s1} + \ldots + V_{s,\,n-1}$, and $V_{d2} = V_{s0} + V_{s1} + \ldots + V_{s,\,n-1}$, with variables corresponding to zero voltage pulses removed; and
      outputting the resulting digital value of each analog voltage pulse.

4. A method for use in positron emission tomography (PET) for digitizing radiation events, comprising:
   comparing each voltage pulse of a group of analog voltage pulses generated by PET detectors with a reference voltage of predetermined energy level of interest such that any analog voltage pulse higher than a reference voltage is kept and any analog voltage pulse lower than the reference voltage is set to zero;
   combining the group of analog voltage pulses to create fewer analog signals than a total number of the analog voltage pulses in the group,
   digitizing the created analog signals; and
   analyzing the digitized signals to obtain a digitized voltage value of each individual analog voltage pulse in the group,
   wherein the digitizing is performed by ADCs and the analyzing further comprises:
      defining the group of analog voltage pulses as $V_0$, $V_1, \ldots, V_{m-1}$, a set of coefficients $\alpha_i = [\alpha_{0,i}, \alpha_{1,i}, \ldots, \alpha_{m-1,i}]^T$, and a set of coefficients $\beta_i = [\beta_{0,i} + \beta_{1,i} + \ldots + \beta_{m-1,i}]^T$, wherein m is an actual precision of the ADCs;
      determining the created analog signals as $V_{d1} = \alpha_0 V_0 + \alpha_1 V_1 + \ldots + \alpha_{m-1} V_{m-1}$, and $V_{d2} = \beta_0 V_0 + \beta_1 V_1 + \ldots + \beta_{m-1} V_{m-1}$;
      removing the variables corresponding to analog voltage pulses set to zero;

determining a digital value of each individual analog voltage pulse $V_i$ by solving equations $V_{d1}=\alpha_0 V_0 + \alpha_1 V_1 + \ldots + \alpha_{m-1} V_{m-1}$ and $V_{d2}=\beta_0 V_0 + \beta_1 V_1 + \ldots + \beta_{m-1} V_{m-1}$ with variables corresponding to zero voltage pulses removed; and outputting the resulting digital value of each analog voltage pulse.

5. A method for use in positron emission tomography (PET) for digitizing radiation events, comprising:

comparing each voltage pulse of a group of analog voltage pulses generated by PET detectors with a threshold reference voltage such that any analog voltage pulse higher than the reference voltage is maintained and any analog voltage pulse lower than the reference voltage is set to zero;

combining the group of analog voltage pulses to create two analog signals, each created analog signal containing information on all of the analog voltage pulses in the group;

digitizing the two created analog signals; and analyzing the two digitized signals to obtain a digitized voltage value of each individual analog voltage pulse in the group, wherein the digitizing is performed by ADCs and the analyzing further comprises:

defining the group of analog voltage pulses as $V_0, V_1, \ldots, V_{n-1}$, wherein $n=1, 2, 4, \ldots, 2^k$ and $k<m-r$, m and r being actual and required precision of the ADCs, respectively, and $m>r$;

determining the two created analog signals as $V_{d1}=V_{s0}+V_{s1}+\ldots+V_{s,\,n-1}$, wherein $V_{s,i}=V_{i+i\times 2^r}$, and $V_{d2}=V_{s0}+V_{s1}+\ldots+V_{s,\,n-1}$, wherein $V_{s,i}=V_i+(n-1-i)\times 2^r$;

removing the variables corresponding to analog voltage pulses set to zero; determining a digital value of each individual analog voltage pulse $V_i$ by solving two equations $V_{d1}=V_{s0}+\ldots+V_{s,\,n-1}$ and $V_{d2}=V_{s0}+\ldots+V_{s,\,n-1}$ with variables corresponding to zero voltage pulses removed; and outputting the resulting digital value of each analog voltage pulse.

6. A method for use in positron emission tomography (PET) for digitizing radiation events, comprising:

comparing each voltage pulse of a group of analog voltage pulses generated by PET detectors with a threshold reference voltage such that any analog voltage pulse higher than the reference voltage is maintained and any analog voltage pulse lower than the reference voltage is set to zero;

combining the group of analog voltage pulses to create two analog signals, each created analog signal containing information on all of the analog voltage pulses in the group;

digitizing the two created analog signals; and analyzing the two digitized signals to obtain a digitized voltage value of each individual analog voltage pulse in the group, wherein the digitizing is performed by ADCs and the analyzing further comprises:

defining the group of analog voltage pulses as $V_0, V_1, \ldots, V_{m-1}$, a set of coefficients $\alpha_i=[\alpha_{0,i}, \alpha_{1,i}, \ldots, \alpha_{m-1,i}]^T$, and a set of coefficients $\beta_i=[\beta_{0,i}+\beta_{1,i}+\ldots+\beta_{m-1,i}]^T$, wherein m is an actual precision of the ADCs;

determining the created analog signals as $V_{d1}=\alpha_0 V_0 + \alpha_1 V_1 + \ldots + \alpha_{m-1} V_{m-1}$, and $V_{d2}=\beta_0 V_0 + \beta_1 V_1 + \ldots + \beta_{m-1} V_{m-1}$;

removing the variables corresponding to analog voltage pulses set to zero; determining a digital value of each individual analog voltage pulse $V_i$ by solving two equations $V_{d1}=\alpha_0 V_0+\alpha_1 V_1+\ldots+\alpha_{m-1} V_{m-1}$ and $V_{d2}=\beta_0 V_0+\beta_1 V_1+\ldots+\beta_{m-1} V_{m-1}$ with variables corresponding to zero voltage pulses removed; and outputting the resulting digital value of each analog voltage pulse.

7. A device for use in positron emission tomography (PET) for digitizing radiation events, comprising:

plural sets of amplifiers, each set of amplifiers coupled to receive a same group of analog voltage pulses generated by PET detectors;

a plurality of adders, each coupled to receive outputs from one set of amplifiers of the plural sets of amplifiers and to sum the outputs into one signal;

a plurality of ADCs, each ADC coupled to receive an output of one of the adders to convert the output into digital form;

an analyzer coupled to receive outputs of the plurality of ADCs to determine a digital voltage value of each individual voltage pulse in the group of analog voltage pulses;

a plurality of comparators coupled to receive the group of analog voltage pulses generated by the PET detectors on respective first inputs, and a reference voltage on respective second inputs;

a plurality of gates, each coupled to receive one of the group of analog voltage pulses and to provide an output to one of the amplifiers in each of the sets of amplifiers, said gates being controlled by respective outputs of the plurality of comparators; and a non-zero selector coupled to receive the respective outputs of the plurality of comparators and to provide to the analyzer information identifying ones of the analog voltage pulses having a zero magnitude.

* * * * *

UNITED STATES PATENT AND TRADEMARK OFFICE
CERTIFICATE OF CORRECTION

| | | |
|---|---|---|
| PATENT NO. | : 7,342,232 B2 | Page 1 of 1 |
| APPLICATION NO. | : 11/097153 | |
| DATED | : March 11, 2008 | |
| INVENTOR(S) | : Qingguo Xie et al. | |

It is certified that error appears in the above-identified patent and that said Letters Patent is hereby corrected as shown below:

Claim 2, column 7, line 63, change "$B_{0,i}$," to -- [$\beta_{0,i}$ --;

Claim 3, column 8, line 29, change "$V_{s,i} = V_i + i \times 2^r$, and $V_{d2} = V_{s0} +$" to -- $V_{s,i} = V_i + i \times 2^r$, and $V_{d2} = V_{s0} +$ --;

Claim 6, column 10, line 12, change "determining the created" to -- determining the two created --;

Claim 6, column 10, line 16, after "pulses set to zero," begin a new paragraph.

Signed and Sealed this

First Day of July, 2008

JON W. DUDAS
*Director of the United States Patent and Trademark Office*